US006455730B1

(12) United States Patent
Chauhan et al.

(10) Patent No.: US 6,455,730 B1
(45) Date of Patent: Sep. 24, 2002

(54) PREPARATION OF DICARBOXYLIC ACID MONOESTERS FROM CYANOCARBOXYLIC ACID ESTERS

(75) Inventors: Sarita Chauhan, Landenburg, PA (US); Robert Dicosimo, Rockland, DE (US); Robert D. Fallon, Elkton, MD (US); John E. Gavagan; Mark S. Payne, both of Wilmington, DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/632,419

(22) Filed: Aug. 4, 2000

(51) Int. Cl.$^7$ .......................... C07C 51/08; C07C 69/76
(52) U.S. Cl. ......................................... 562/484; 560/76
(58) Field of Search ............................. 562/484; 560/76

(56) References Cited

U.S. PATENT DOCUMENTS

| 5,629,190 A | 5/1997 | Petre et al. |
| 5,814,508 A | 9/1998 | Di Cosimo et al. |
| 5,858,736 A | 1/1999 | Di Cosimo et al. |
| 5,998,180 A | 12/1999 | Armitage et al. |

FOREIGN PATENT DOCUMENTS

| WO | WO 9837219 | 8/1996 |
| WO | WO 00/23577 | 4/2001 |

OTHER PUBLICATIONS

Rounds et al., Tetrahedron Lett. (1988) 29, 6557.
Almatawah et al., Extremophiles (1999) 3: 283–291.
Kobayashi et al., Tetrahedron (1990) 46, 5587–5590.
J. Bacteriology (1990) 172, 4807–4815.
S. Levy–Schil et al., Gene (1995) 161, 15–20.
C. Bengis–Garber, A. L. Gutman, Appl. Micribiol. Biotechnol. (1989) 32, 11.
M. L. Gradley, C. J. Knowles, Biotechnology Lett. (1994) 16, 41.
Bhalla et al., Appl. Micribiol. Biotechnol. (1992) 37, 184.
A. Goldlust, J. Bohak, Biotechnol. Appl. Biochem. (1989) 11, 581.
K. Yamamoto et al., Agric. Biol. Chem (1991) 55, 1459.
Yamamoto et al., J. Ferment Bioeng. (1992) 73, 425.
Gavagan et al., J. Org. Chem. (1998)63, 4792.
Pollett et al., Synthesis (1978) 2, 142–143.
de Raadt et al., J. Chem. Soc. Perkins Trans. I, (1992) 1, 137–140.
Klempier et al., Food Technol. Biotechnol. (1996) 34, 67–70.

*Primary Examiner*—Paul J. Killos

(57) ABSTRACT

This invention relates to a process for preparing dicarboxylic acid monoesters from cyanocarboxylic acid esters. More particularly, using the nitrilase from *Acidovorax facilis* 72W (ATCC 55745) in various forms as an enzyme catalyst, an aliphatic or aromatic cyanocarboxylic acid ester is converted to the corresponding dicarboxylic acid monoester with high chemoselectivity at 100% conversion. An embodiment of the invention also provides a process for obtaining high chemoselectively and high regioselectivity.

20 Claims, No Drawings

PREPARATION OF DICARBOXYLIC ACID MONOESTERS FROM CYANOCARBOXYLIC ACID ESTERS

FIELD OF THE INVENTION

This invention relates to a process for preparing dicarboxylic acid monoesters from cyanocarboxylic acid esters. More particularly, the nitrilase from *Acidovorax facilis* 72W catalyzes the conversion of an aliphatic or aromatic cyanocarboxylic acid ester to the corresponding dicarboxylic acid monoester with high chemoselectivity at 100% conversion.

BACKGROUND

Nitriles are readily converted to the corresponding carboxylic acids by a variety of chemical processes, but these processes typically require strongly acidic or basic reaction conditions and high reaction temperatures, and usually produce unwanted byproducts and/or large amounts of inorganic salts as unwanted waste. The reaction conditions used to chemically hydrolyze nitriles will usually also hydrolyze any ester functional groups also present in the molecule. For example, the chemoselective hydrolysis of aromatic or aliphatic cyanocarboxylic acid esters by tetrahalophthalic acids produces the corresponding dicarboxylic acid monoesters in 56% to 65% yields, and the use of an equimolar quantity of tetrahalophthalic acid generated an undesirable reaction byproduct (Rounds et al., *Tetrahedron Lett.* (1988) 29, 6557). The enzyme-catalyzed hydrolysis of nitrile-containing substrates to the corresponding carboxylic acids is often preferred to chemical methods because the reactions 1) are often run at ambient temperature, 2) do not require the use of strongly acidic or basic reaction conditions, and 3) produce the desired product with high selectivity at high conversion.

A nitrilase enzyme directly converts a nitrile to the corresponding carboxylic acid and ammonia in an aqueous reaction mixture without the intermediate formation of an amide. A stereospecific nitrilase of *Alcaligenes faecalis* has been used to resolve racemic nitriles in the manufacture of chiral carboxylic acids, and the gene encoding the nitrilase has been cloned and expressed (WO 00/23577). A nitrilase has been isolated from the thermophilic bacterium *Bacillus pallidus* strain Dac521 that catalyzed the hydrolysis of aliphatic, aromatic, and heterocyclic nitrites (Almatawah et al., *Extremophiles* (1999) 3:283–291). A nitrilase from *Rhodococcus rhodochrous* NCIMB 40757 or NCIMB 40833 has been used to convert acrylonitrile to ammonium acrylate (U.S. Pat. No. 5,998,180). Kobayashi et al. (Tetrahedron (1990) 46, 5587–5590; *J. Bacteriology* (1990) 172, 4807–4815) have described an aliphatic nitrilase isolated from *Rhodococcus rhodochrous* K22 that catalyzed the hydrolysis of a variety of aliphatic nitriles to the corresponding carboxylic acid ammonium salts. A nitrilase from *Comamonas testosteroni* has been isolated that can convert a range of aliphatic α,ω-dinitriles to either the corresponding ω-cyanonitrilecarboxylic acid ammonium salt or dicarboxylic acid diammonium salt (CA 2,103,616; S. Levy-Schil et al., Gene (1995) 161, 15–20).

Nitrilases are also produced by *Rhodococcus rhodochrous* NCIMB 11216 (C. Bengis-Garber, A. L. Gutman, *Appl. Microbiol. Biotechnol.* (1989) 32, 11; M. L. Gradley, C. J. Knowles, *Biotechnology Lett.* (1994) 16, 41), *Rhodococcus rhodochrous* PA-34 (Bhalla et al., *Appl. Microbiol. Biotechnol.* (1992) 37, 184), *Fusarium oxysporum* f. sp. melonis (A. Goldlust, Z. Bohak, *Biotechnol. Appl. Biochem.* (1989) 11, 581), *Acinetobacter sp. AK*226 (K. Yamamoto, K. Komatsu, *Agric. Biol. Chem.* (1991) 55, 1459), *Acidovorax facilis* ATCC8750 (Yamamoto et al., *J. Ferment. Bioeng.* (1992) 73, 425), and *Acidovorax facilis*72W (Gavagan et al., *J. Org. Chem.* (1998) 63, 4792).

The ability to chemoselectively convert a nitrile functional group to the corresponding carboxylic acid is a powerful tool for the preparation of agrochemicals and pharmaceuticals. These industries have a need to prevent losses in yield from hydrolysis of functional groups other than nitriles. Eliminating protection and deprotection of other hydrolyzable functional groups such as esters, acetals, or epoxides would bring an additional benefit to industry.

Propanedioic acid monoethyl ester (commonly known as ethyl hydrogen malonate or monoethylmalonate) is a useful bifunctional building block (see, for example, Pollett et al., *Synthesis* (1978) 2, 142–143). Monoethylmalonate has been prepared by hydrolysis of cyanoacetic acid ethyl ester using Corynebacterium, Gordona, or Rhodococcus cells having nitrilase activity (WO 9837219): *G. terrae* MA-1 gave a yield of monoethylmalonate of 89.9%. This method is touted as superior in yield and cost to both the chemical hydrolysis of diethylmalonate and the regioselective enzymatic hydrolysis of diethylmalonate using esterases.

Not all nitrile-hydrolyzing enzymes (either as contained in microbial cell catalysts or as isolated enzymes) can chemoselectively hydrolyze a cyanocarboxylic acid ester nitrile group to produce the corresponding dicarboxylic acid monoester. In the process, the ester may also be hydrolyzed or the chemoselectivity of the enzyme may be specific to the particular cyanocarboxylic acid ester reactant. An immobilized enzyme preparation from Rhodococcus sp. has been examined for the chemoselective hydrolysis of cyanocarboxylic acid esters (de Raadt et al., *J. Chem Soc. Perkins Trans. I,* (1992) 1, 137–140); 2-cyanoethylpropanedioic acid diethyl ester was chemoselectively hydrolyzed to 1,1,3-propanetricarboxylic acid diethyl ester in 92% yield, whereas under the same conditions 5-cyanopentanoic acid methyl ester was completely converted with no chemoselectivity to adipic acid (complete ester and nitrile hydrolysis). Resting cells of *Rhodococcus rhodochrous* NCIMB 11216 have been examined for the chemoselective hydrolysis of cyanocarboxylic acid esters (Klempier et al., *Food Technol. Biotechnol.* (1996) 34, 67–70), and with this catalyst 2-cyanoethyl-propanedioic acid diethyl ester was chemoselectively hydrolyzed to 1,1,3-propanetricarboxylic acid diethyl ester in 56% yield (20% 2-cyanoethyl-propanedioic acid monoethyl ester was also produced), whereas under the same conditions 5-cyanopentanoic acid methyl ester was completely converted with no chemoselectivity to 5-cyanovaleric acid (complete ester hydrolysis with no nitrile hydrolysis). For the hydrolysis of 4-cyanobenzoic acid methyl and ethyl esters, *R. rhodochrous* NCIMB 11216 (Klempier et al. supra) produced the corresponding 1,4-benzenedicarboxylic acid esters in 79% and 42% yields at 100% conversion, respectively, with ester hydrolysis products accounting for the remaining reaction byproducts.

U.S. Pat. No. 5,858,736 describes the use of the nitrilase activity of a microbe, *Acidovorax facilis* 72W (ATCC 55746), as a catalyst for the hydrolysis of aliphatic α,ω-dinitriles to the corresponding ω-cyanocarboxylic acids and ammonia in an aqueous reaction mixture. The nitrilase was found to be highly regioselective, where hydrolysis of an α-alkyl-α,ω-dinitrile produced only the ω-cyanocarboxylic acid resulting from hydrolysis of the ω-nitrile group. U.S. Pat. No. 5,814,508 describes a process whereby heating a suspension of *Acidovorax facilis* 72W (ATCC 55746) in a suitable buffer at 50° C. for a short period of time deactivates an undesirable nitrile hydratase and amidase activity of the whole-cell catalyst, without producing a significant decrease in the desired nitrilase activity.

The problem to be solved remains the lack of a facile enzymatic catalyst for chemoselective hydrolysis of nitrile functional groups in the presence of other hydrolyzable functional groups, with high yield and high selectivity and with the added advantages of low temperature requirements and low waste.

SUMMARY OF THE INVENTION

A process is disclosed for preparing aliphatic or aromatic dicarboxylic acid monoesters from aliphatic or aromatic cyanocarboxylic acid esters. The invention has the steps of (a) contacting an aliphatic or aromatic cyanocarboxylic acid ester in an aqueous reaction mixture with an enzyme catalyst characterized by a chemoselective nitrilase activity derived from *Acidovorax facilis* 72W; and (b) isolating the aliphatic or aromatic dicarboxylic acid monoester produced in (a). More particularly, an aliphatic or aromatic cyanocarboxylic acid ester is converted to the corresponding dicarboxylic acid monoester with high chemoselectivity at 100% conversion, using as an enzyme catalyst the nitrilase from *Acidovorax facilis* 72W (ATCC 55746).

Further embodiments of the invention use an enzyme catalyst having nitrilase activity in the form of whole microbial cells, permeabilized microbial cells, one or more cell components of a microbial cell extract, and partially purified enzyme(s), or purified enzyme(s). These different forms of enzyme catalyst can be immobilized on or in a soluble or insoluble support using techniques well-known to those skilled in the art. Microorganisms characterized by a nitrilase activity and useful in the process are *Acidovorax facilis* 72W (ATCC 55746) and its mutants, *Acidovorax facilis* 72-PF-15 (ATCC 55747), and *Acidovorax facilis* 72-PF-17 (ATCC 55745). Additionally, transformed microbial cells containing *A. facilis* nitrilase activity are included in this invention. *Escherichia coli* SS 1001 (ATCC PTA-1177) and *Escherichia coli* SW91 (ATCC PTA-1175) are examples of such a transformed microbial cell catalyst.

A further embodiment of the invention is the use of whole microbial cells, preferably the *A. facilis* 72W strains set out above and transformed microbial cells containing *A. facilis* 72W nitrilase activity, characterized by (1) a regioselective and chemoselective nitrilase activity and (2) a non-regioselective nitrile hydratase and amidase activity, as an enzyme catalyst for the conversion of cyanocarboxylic acid esters to the corresponding dicarboxylic acid monoesters, where prior to use as catalyst, the whole microbial cells are heated to a temperature of about 35° C. to 70° C. for between 10 and 120 minutes, wherein the non-regioselective nitrile hydratase and amidase activity is destroyed and the regioselective nitrilase activity is preserved. Where the transformed whole microbial cell lacks the non-regioselective nitrile hydratase and amidase activities, no heat-treatment step is needed. *Escherichia coli* SS1001(ATCC PTA-1177) and *Escherichia coli* SW91 (ATCC PTA-1175) are examples of a transformed microbial cell catalyst that lacks non-regioselective nitrile hydratase and amidase activities. In either case and optionally, the enzyme catalyst may be immobilized on a soluble or insoluble support.

A further embodiment of the invention uses an aliphatic cyanocarboxylic acid ester with the formula $R_3O_2C(CR_1R_2)_nCH_2CN$, where n=0 to 16, $R_1$ and $R_2$ for each $(CR_1R_2)$ unit are individually selected from the group consisting of hydrogen, hydroxyl, alkoxyl, aryloxyl, unsubstituted or substituted alkyl, unsubstituted or substituted alkenyl, unsubstituted or substituted alkylidene, unsubstituted or substituted alkylaryl, unsubstituted or substituted aryl, alkoxycarboxyl, or aryloxycarboxyl, and where $R_3$ is selected from the group consisting of unsubstituted or substituted alkyl, alkylaryl, or aryl.

A further embodiment of the invention uses as a substrate an aromatic cyanocarboxylic acid ester with the formula:

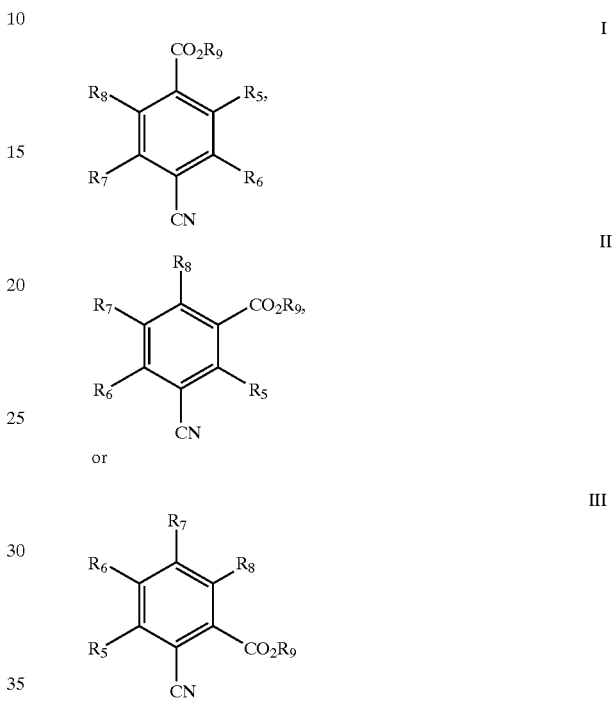

where $R_5$, $R_6$, $R_7$ and $R_8$ are individually selected from the group consisting of hydrogen, hydroxyl, alkoxyl, aryloxyl, unsubstituted or substituted alkyl, unsubstituted or substituted alkenyl, unsubstituted or substituted alkylaryl, unsubstituted or substituted aryl, alkoxycarboxyl, or aryloxycarboxyl, and where $R_9$ is selected from the group consisting of unsubstituted or substituted alkyl, alkylaryl, or aryl.

BRIEF DESCRIPTION OF THE BIOLOGICAL DEPOSITS

Applicants have made the following biological deposits under the terms of the Budapest Treaty on the International Recognition of the Deposit of Micro-organisms for the purposes of Patent Procedure:

| Depositor Identification Reference | Int'l. Depository Designation | Date of Deposit |
|---|---|---|
| *Acidovorax facilis* 72-PF-17 | ATCC 55745 | 8 March 1996 |
| *Acidovorax facilis* 72W | ATCC 55746 | 8 March 1996 |
| *Acidovorax facilis* 72-PF-15 | ATCC 55747 | 8 March 1996 |
| *Escherichia coli* SS1001 | ATCC PTA-1177 | 11 January 2000 |
| *Escherichia coli* SW91 | ATCC PTA-1175 | 11 January 2000 |

As used herein, "ATCC" refers to the American Type Culture Collection International Depository Authority located at ATCC, 10801 University Blvd., Manassas, Va. 20110–2209, USA. The "International Depository Designation" is the accession number to the culture on deposit with ATCC.

DETAILED DESCRIPTION OF THE INVENTION

The listed deposits will be maintained in the indicated international despository for at least thirty (30) years and will be made available to the public upon the grant of a patent disclosing it. The availability of the deposit does not constitute a license to practice the subject invention in derogation of patent rights granted by government action.

A process to chemoselectively prepare aliphatic or aromatic dicarboxylic acid monoesters from the corresponding cyanocarboxylic acid esters in high yields has been developed that uses the nitrilase activity of *Acidovorax facilis* 72W. A nitrilase enzyme directly converts an aliphatic or aromatic nitrile to the corresponding carboxylic acid, without the formation of the corresponding amide intermediate (equation 1):

Equation 1.

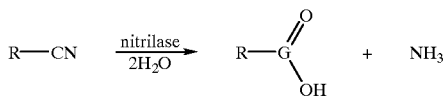

There are currently no non-enzymatic methods for the chemoselective hydrolysis of an aliphatic or aromatic cyano group of a cyanocarboxylic acid ester that can produce the high yields and selectivities to dicarboxylic acid monoesters obtained using enzyme catalysis. Non-enzymatic nitrile hydrolysis reactions typically involve heating soultions of the nitrile at elevated temperatures (often in the presence of strong acid or base). In contrast, the enzyme-catalyzed reactions described above are carried out at ambient temperature in an aqueous reeaction mixture and at neutraal pH with no added acid or base.

The dicarboxylic acid monoesters produced by the present invention are useful as precursors for chemicals of high value in the agricultural and pharmaceutical industries. In addition to the utility of these precursors in forming desirable compounds, the invention also provides a number of processing advantages relative to previously-known chemical processes. The claimed invention generates little waste and permits a facile approach to product recovery. The process uses temperatures below 70° C. to obtain a high yield of dicarboxylic acid monoester when using water as a solvent.

It has now been discovered, and it is the subject of the present invention, that in addition to being highly regioselective, the nitrilase present in *Acidovorax facilis* 72W (ATCC 55746) is highly chemoselective, and can be used to selectively hydrolyze nitrile functional groups in the presence of ester functional groups.

Heat-treatment of suspensions of *Acidovorax facilis* 72W (ATCC 55746) at about 50° C. for one hour produces a microbial whole-cell catalyst that hydrolyzes specific substrates with extremely high chemoselectivity. At complete conversion of cyanocarboxylic acid ester, at least a 97% yield of the aliphatic dicarboxylic acid monoester is produced, and at least a 94% yield of the aromatic dicarboxylic acid monoester is produced as shown in Table 1.

TABLE 1

| cyanocarboxylic acid ester (substrate) | concentration (M) (substrate) | dicarboxylic acid monoester (product) | yield (%) |
|---|---|---|---|
| cyanoacetic acid ethyl ester | 0.10 (Example 11) | propanedioic acid monoethyl ester | 100 |
| | 0.40 (Example 12) | | 100 |
| cyanoacetic acid propyl ester | 0.40 (Example 13) | propanedioic acid monopropyl ester | 100 |
| 3-cyanopropanoic acid methyl ester | 0.40 (Example 3) | butanedioic acid monomethyl ester | 99 |
| | 1.00 (Example 5) | | 100 |
| | 2.00 (Example 6) | | 100 |
| 5-cyanopentanoic acid methyl ester | 0.10 (Example 9) | hexanedioic acid monomethyl ester | 99 |
| | 1.00 (Example 10) | | 97 |
| 4-cyanobenzoic acid methyl ester | 0.052 (Example 14) | 1,4-benzene dicarboxylic acid monomethyl ester | 94 |

Similar percent yields of dicarboxylic acid monoesters have also been obtained using purified *A. facilis* 72W nitrilase, cell extracts of *A. facilis* 72W, whole cells of *A. facilis* 72W including permeabilized cells and transformed cells containing *A. facilis* 72W nitrilase activity, as described in the accompanying Examples.

Two mutants of the *Acidovorax facilis* 72W (ATCC 55746) strain have been prepared (U.S. Pat. No. 5,858,736) that produce only very low levels of the undesirable nitrile hydratase activity responsible for non-regioselective nitrile hydrolysis of aliphatic dinitriles. These mutant strains, *Acidovorax facilis* 72-PF-15 (ATCC 55747) and *Acidovorax facilis* 72-PF-17 (ATCC 55745), do not require heat-treatment of the cells before use as a catalyst to hydrolyze an aliphatic or aromatic cyanocarboxylic acid ester to the corresponding dicarboxylic acid monoester. These mutants are expected to be operable in this chemoselective invention. In cases where the regioselectivity of the nitrilase is not required, the *Acidovorax facilis* 72W (ATCC 55746) strain does not have to be heat treated in order to deactivate the non-regioselective nitrile hydratase activity (see Examples 3 and 4).

Transformation and Expression of Nitrilase Genes

Heterologous expression of nitrilase activity from transformed hosts has been reported (Kobayashi et al. 1993, *Proc. Nat. Acad. Sci.* 90:247; Kobayashi et al. 1992. *J. Biol. Chem.* 267:20746; Kobayashi et al. 1992 *Biochem.* 31:9000–9007; U.S. Pat. No. 4,810,648). In some cases the hosts must be specifically modified in order to express good enzyme activity (Levy-Schil et al. 1995 *Gene* 161:15–20; U.S. Pat. No. 5,830,693; U.S. Pat. No. 5,635,391). In cases where good nitrilase activity is found, the enzyme expressed by the transformed host retains the nitrile hydration activity of the native enzyme. Microorganisms transformed so as to include the nitrilase activity of *Acidovorax facilis* 72W (for instance, *Escherichia coli* SS1001 (ATCC PTA-1177) or *Escherichia coli* SW91 (ATCC PTA-1175)) may also be used as catalyst in the present invention. Definitions:

In the application, unless specifically stated otherwise, the following abbreviations and definitions apply:

The abbreviations in the specification correspond to units of measure, techniques, properties, or compounds as follows: "sec" means second(s), "min" means minute(s), "h"

means hour(s), "d" means day(s), "μL" means microliter, "mL" means milliliters, "L" means liters, "mM" means millimolar, "M" means molar, "mmol" means millimole(s), "Ampr" means ampicillin resistance, "Amps" means ampicillin sensitivity, "kb" means kilo base, "kd" means kilodaltons, "nm" means nanometers, and "wt" means weight. "ORF" means "open reading frame, "PCR" means polymerase chain reaction, "HPLC" means high performance liquid chromatography, "ca" means approximately, "O.D." means optical density at the designated wavelength, "IU" means International Units, "wcw" means wet cell weight, "dcw" means dry cell weight.

"PMSF" refers to phenylmethylsulfonyl floride.

"Enzyme catalyst" or "whole microbial cell catalyst" refers to a catalyst that is characterized by a nitrilase activity. The enzyme catalyst may be in the form of a whole microbial cell, permeabilized microbial cell(s), one or more cell components of a microbial cell extract, partially purified enzyme(s), or purified enzyme(s).

"Chemoselective" refers to a reaction where one functional group of a molecule (e.g., a nitrile group) is selectively reacted in the presence of one or more different functional groups (e.g., ester and/or epoxide groups). Chemoselectivity is the preferential reaction of a chemical reagent, catalyst or enzyme with one of two or more different functional groups. A reagent is highly chemoselective if the reaction occurs at only one of a limited number of different functional groups.

"Regioselective reaction" refers to a reaction that can produce two or more structural isomers, but produces only one exclusively or predominantly. Reactions are termed completely (100%) regioselective if the discrimination is complete, or partially (x %) regioselective, if the product of reaction at one site predominates over the product of reaction at other sites. The discrimination may also semi-quantitatively be referred to as high or low regioselectivity.

The terms "*Acidovorax facilis*" and "*A. facilis*" are used interchangeably.

The terms "*Escherichia coli*" and "*E. coli*" are used interchangeably.

DESCRIPTION OF THE PREFERRED EMBODIMENTS

Methods and Materials

Growth of *Acidovorax facilis* strain 72W (ATCC 55746)

One frozen seed lot vial of *Acidovorax facilis* strain 72W (ATCC 55746) was thawed and the 1 mL contents placed in 500 mL of sterile Inoculum Medium listed below. The inoculum was grown at 30° C. with shaking at 250 rpm in a two liter flask for 24–30 h.

Inoculum Medium

| Component: | Final Concentration: |
|---|---|
| Potassium phosphate, monobasic | 1.5 g/L |
| Potassium phosphate, dibasic | 3.4 g/L |
| Ammonium sulfate | 1.5 g/L |
| Trisodium citrate, dihydrate | 1 g/L |
| Magnesium sulfate, heptahydrate | 0.4 g/L |
| Trace metal solution (below) | 1 mL/L |
| Amberex 695 (Universal Foods) | 1 g/L |
| Glycerol (sterilized separately) | 8 g/L |

Trace Metal Solution

| Component: | Stock Concentration: |
|---|---|
| Hydrochloric Acid | 10 mL/L |
| Calcium chloride, dihydrate | 11.4 g/L |
| Manganese Sulfate, monohydrate | 1.23 g/L |
| Copper sulfate, pentahydrate | 0.63 g/L |
| Cobalt chloride, hexahydrate | 0.16 g/L |
| Boric Acid | 0.91 g/L |
| Zinc sulfate, heptahydrate | 1.77 g/L |
| Sodium molybdate, dihydrate | 0.05 g/L |
| Vanadyl sulfate, dihydrate | 0.08 g/L |
| Nickel nitrate, hexahydrate | 0.04 g/L |
| Sodium selenite | 0.04 g/L |
| Ferrous sulfate, heptahydrate | 6.0 g/L |

The inoculum from the shake flask was transferred aseptically to a presterilized Braun Biostat C fermenter containing Fermenter Medium listed below. Growth occurred under the following conditions: 32° C., pH 6.8–7.0, dissolved oxygen at 25% of saturation. At inoculation the fermenter contained 8.5 liters of Fermenter Medium plus 218 g of Nutrient Feed solution, giving a starting concentration of approximately 7 g/L glycerol. The Nutrient Feed solution includes the following components that were sterilized separately and combined after cooling: potassium phosphate, monobasic, 19.6 g in 0.25 liters deionized water; magnesium sulfate, heptahydrate, 3.3 g, plus sulfuric acid, 4 mL, in 0.15 liters deionized water; Trace Metal solution, 67 mL, plus 400 g glycerol in 0.80 liters deionized water. At 18 hours post inoculation, feeding of Nutrient Feed solution began. Initially, the Nutrient Feed solution was added at a rate of 0.4 g feed/minute (0. 15 g glycerol/min). The culture OD 550 was approximately 8–9. At 26 hours, the feed rate was increased to 0.9 g feed/minute (0.3 g glycerol/min). The OD 550 was approximately 16–18. A final increase in feed rate to 1.8 g feed/minute (0.6 g glycerol/min) was made at 34 hours. This rate continued to the end of run (about 42 hours). The final OD 550 was approximately 65–75.

Fermenter Medium

| Component: | Final Concentration: |
|---|---|
| Potassium phosphate, monobasic | 0.39 g/L |
| Potassium phosphate, dibasic | 0.39 g/L |
| Difco yeast extract | 5.0 g/L |

Cells, as wet cell paste, were recovered by centrifugation and stored frozen until use. Dry cell weight of wet cell paste, obtained by lyophilization, was typically 24% of wet cell weight. For use as a biocatalyst, *Acidovorax facilis* 72W (ATCC 55746) cells were optionally heated to 50° C. for 1 h in 0.35 M phosphate buffer (pH 7.0) before use as catalyst to inactivate nitrile hydratase activity.

The whole cells may be permeabilized by methods familiar to those skilled in the art (e.g., treatment with toluene, detergents, or freeze-thawing) to improve the rate of diffusion of materials into and out of the cells.

Preparation of Cell Extract and Purification of Nitrilase Protein

All steps in this procedure were performed at 5° C. and at pH 7.5 unless otherwise stated.

A 25 wt % suspension of *Acidovorax facilis* 72W (ATCC 55746) wet cell paste was prepared in 20 mM Tris buffer, pH 7.5, 0.1 mM phenylmethylsulfonyl fluoride (PMSF), and 2.0 mM dithiothreitol.

An extract of this suspension was prepared by passage through a French press (American Instrument Co., Silver Springs, Md., USA) according to methods known to the art. Following a centrifugation at 27,500 ×g for 30 minutes to remove cell debris, a 20–55% ammonium sulfate fractionation of the extract was prepared and then concentrated by overnight precipitation following the addition of solid ammonium sulfate to 65% of saturation. The concentrated protein precipitate was reconstituted using a minimum volume of 20 mM Tris, pH 7.5 (Buffer A) and desalted over a PD10 column containing Sephadex G-25 resin (Pharmacia). Following desalting, the concentrated protein extract was fractionated by anion exchange chromatography using a column containing 50 mL of Q-Sepharose fast flow (Pharmacia). After loading the column with the concentrated protein extract, the column was washed with three column volumes of Buffer A at a flow rate of 2 mL/min to remove un-adsorbed protein. Adsorbed protein was eluted from the column using a 0–0.5 M NaCl gradient prepared in Buffer A. Elution of protein from the column was monitored at 280 nm.

Nitrilase activity was monitored throughout purification using an assay measuring the hydrolysis of benzonitrile to produce benzoic acid (Gavagan et al., *Appl. Microbiol. Biotechnol.* (1999) 52, 654–659). Nitrilase activity eluted at 0.4 M NaCl. Protein components in the 0.4 M NaCl protein fraction were separated by gel electrophoresis (SDS-PAGE) performed under reducing conditions (5% β-mercaptoethanol) on a 10–15% SDS polyacrylamide gel. Greater than 50% of the 0.4 M NaCl protein fraction consisted of a protein with subunit molecular weight of 39.7 kd. Using methods known to the art, the native molecular weight of the nitrilase was determined to be 570 kd following gel filtration chromatography in 20 mM phosphate buffer at pH 7 using a Hiload 16/60 Superdex 200 column (Pharmacia) that had been calibrated using gel filtration MW standards (Pharmacia # 17–0442–01). Following gel filtration, the nitrilase protein was >90% pure. The specific activity of the purified enzyme was determined to be 35 IU/mg protein using 2-methylglutaronitrile as substrate at 25° C.

Aliphatic or Aromatic Cyanocarboxylic Acid Ester Hydrolysis Reactions

An aqueous reaction mixture containing the aliphatic or aromatic cyanocarboxylic acid ester is prepared by mixing, the cyanocarboxylic acid ester with an aqueous suspension of the appropriate enzyme catalyst. Whole microbial cells can be used as catalyst without any pretreatment such as permeabilization or heating,. Alternatively, they can be immobilized in a polymer matrix (e.g.,., alginate beads or polyacrylamide gel (PAG) particles) or on a soluble or insoluble support (e.g.,., celite) to facilitate recovery and reuse of the catalyst. Methods for the immobilization of cells in a polymer matrix or on a soluble or insoluble support have been widely reported and are well-known to those skilled in the art. The nitrilase enzyme can also be isolated from the whole cells and used directly as catalyst, or the nitrilase can be immobilized in a polymer matrix or on a soluble or insoluble support. These methods have also been widely reported and are well-known to those skilled in the art (Methods in Biotechnology, Vol. 1: Immobilization of Enzymes and Cells; Gordon F. Bickerstaff, Editor; Humana Press, Totowa, N.J., USA; 1997).

Some of the aliphatic or aromatic cyanocarboxylic acid esters used as starting material in the present invention are only moderately water soluble. Their solubility also depends on the temperature of the solution and the salt (buffer) concentration in the aqueous phase. In this case, producing an aqueous reaction mixture containing an aromatic or aliphatic dicarboxylic acid monoester at a concentration greater than the solubility limit of the starting cyanocarboxylic acid ester is accomplished using a reaction mixture that is initially composed of two phases: an aqueous phase (containing the enzyme catalyst and dissolved aliphatic or aromatic cyanocarboxylic acid ester) and an organic phase (the undissolved aliphatic or aromatic cyanocarboxylic acid ester). As the reaction progresses, the aliphatic or aromatic cyanocarboxylic acid ester dissolves into the aqueous phase, eventually yielding a single phase product mixture. The aqueous phase of a two-phase reaction mixture can contain, at a minimum, only as much water as is sufficient to result in a) complete conversion of the aliphatic or aromatic cyanocarboxylic acid ester to the corresponding dicarboxylic acid monoester, and b) maintenance of the hydrolytic activity of the enzyme catalyst. The reaction may also be run by adding the aliphatic or aromatic cyanocarboxylic acid ester to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

The final concentration of aliphatic or aromatic dicarboxylic acid monoester in the product mixture at complete conversion of the corresponding aliphatic or aromatic cyanocarboxylic acid ester may range from 0.001 M to the solubility limit of the aliphatic or aromatic dicarboxylic acid monoester. Typically, the concentration of the aliphatic or aromatic dicarboxylic acid monoester ranged from 0.10 M to 2.0 M. The aliphatic or aromatic dicarboxylic acid monoester may also be isolated from the product mixture (after removal of the catalyst) by adjusting the pH of the reaction mixture to between 2.0 and 2.5 with concentrated HCl, saturating the resulting solution with sodium chloride, and extracting the aliphatic or aromatic dicarboxylic acid monoester with a suitable organic solvent such as ethyl acetate, ethyl ether, or dichloromethane. The organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

The concentration of enzyme catalyst in the reaction mixture depends on the specific catalytic activity of the enzyme catalyst and is chosen to obtain the desired rate of reaction. The wet cell weight of the microbial cells used as catalyst in hydrolysis reactions typically ranges from 0.001 grams to 0.100 grams of wet cells per mL of total reaction volume, preferably from 0.002 grams to 0.050 grams of wet cells per mL. The specific activity of the microbial cells (IU/gram wet cell wt.) is determined by measuring the rate of conversion of a 0.10 M solution of a cyanocarboxylic acid ester substrate to the desired dicarboxylic acid monoester product at 25° C., using a known weight of microbial cell catalyst. An IU of enzyme activity is defined as the amount of enzyme activity required to convert one micromole of substrate to product per minute.

The temperature of the hydrolysis reaction is chosen to optimize both the reaction rate and the stability of the enzyme catalyst activity. The temperature of the reaction may range from just above the freezing point of the suspension (ca. 0° C.) to 70° C., with a preferred range of reaction temperature of from 5° C. to 35° C. The microbial cell catalyst suspension may be prepared by suspending the cells in distilled water, or in an aqueous reaction mixture of a buffer that will maintain the initial pH of the reaction between 5.0 and 10.0, preferably between 6.0 and 8.0. As the reaction proceeds, the pH of the reaction mixture may change due to the formation of an ammonium salt of the carboxylic acid from the corresponding nitrile functionality of the cyanocarboxylic acid ester. The reaction can be run to complete conversion of cyanocarboxylic acid ester with no pH control, or a suitable acid or base can be added over the course of the reaction to maintain the desired pH.

In the following examples, that serve to further illustrate the invention and not to limit it, the % recovery of aliphatic cyanocarboxylic acid esters and the % yields of the hydrolysis products formed during the microbial hydrolysis reactions were based on the initial amount of aliphatic cyanocarboxylic acid esters present in the reaction mixture, and determined by HPLC using a refractive index detector and a Supelcosil LC-18-DB column (15 cm×4.6 mm diameter). The yields of 1,4-benzenedicarboxylic acid monomethyl ester and hydrolysis products formed during the microbial hydrolysis reactions were based on the initial amount of the aromatic cyanocarboxylic acid ester present in the aqueous reaction mixture, and determined by gas chromatography using a HP-5 capillary column (30 m×0.32 mm ID, 0.25 micron film thickness).

EXAMPLE 1

Butanedioic acid monomethyl ester

Into a 10-mL volumetric flask was added 0.4586 g (4.05 mmol, 0.405 M) of 3-cyanopropanoic acid methyl ester, 9.08 mL of potassium phosphate buffer (50 mM, pH 7.0), and 0.50 mL of an aqueous solution containing 22.9 mg/mL of purified nitrilase (isolated from *Acidovorax facilis* 72W (ATCC 55746) cells) in 20 mM HEPES buffer (pH 7.5, containing 1 mM dithiothreitol and 0.1 mM EDTA), and the resulting 10 mL solution stirred at 25° C. Samples (0.100 mL) were mixed with 0.300 mL of distilled water, centrifuged, then 0.360 mL of the 1:4 diluted supernatant was mixed with 0.040 mL of 0.750 M N-methylpropionamide (HPLC external standard solution). The resulting solution was analyzed by HPLC. After 6.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 2

Butanedioic acid monomethyl ester

An 82.2 mg (dry cell weight)/mL aqueous cell extract (prepared from *Acidovorax facilis* 72W (ATCC 55746) cells) in 100 mM potassium buffer (pH 7.0, containing 1 mM dithiothreitol and 0.1 mM PMSF) was heated at 50° C. for 25 min, then cooled to 25° C. Into a 10-mL volumetric flask was added 0.4577 g (4.05 mmol, 0.405 M) of 3-cyanopropanoic acid methyl ester, 9.28 mL of potassium phosphate buffer (50 mM, pH 7.0), and 0.30 mL of the heat-treated 82.2 mg (dry cell weight)/mL aqueous cell extract, and the resulting 10 mL solution stirred at 25° C. Samples (0.100 mL) were mixed with 0.300 mL of distilled water, centrifuged, then 0.360 mL of the 1:4 diluted supernatant was mixed with 0.040 mL of 0.750 M N-methylpropionamide (HPLC external standard solution). The resulting solution was analyzed by HPLC. After 6.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 3

Butanedioic acid monomethyl ester

Into a 10-mL volumetric flask was added 0.4536 g (4.01 mmol, 0.401 M) of 3-cyanopropanoic acid methyl ester, 9.38 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1h), and the resulting 10 mL suspension stirred at 25° C. Samples (0.100 mL) were mixed with 0.300 mL of distilled water, centrifuged, then 0.180 mL of the 1:4 diluted supernatant was mixed with 0.020 mL of 0.750 M N-methylpropionamide (HPLC external standard solution). The resulting solution was analyzed by HPLC. After 4.0 h, the conversion of 3-cyanopropanoic acid methyl ester was complete, and the yield (determined by HPLC) of butanedioic acid monomethyl ester was 99%, with no production of 3-cyanopropionic acid or butanedioic acid.

EXAMPLE 4

Butanedioic acid monomethyl ester

Into a 10-mL volumetric flask was added 0.4515 g (3.99 mmol, 0.399 M) of 3-cyanopropanoic acid methyl ester, 9.38 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, no heat-treatment of cell suspension at 50° C. prior to addition), and the resulting 10 mL suspension stirred at 25° C. Samples (0.100 mL) were mixed with 0.300 mL of distilled water, centrifuged, then 0.180 mL of the 1:4 diluted supernatant was mixed with 0.020 mL of 0.750 M N-methylpropionamide (HPLC external standard solution). The resulting solution was analyzed by HPLC. After 5.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 5

Butanedioic acid monomethyl ester

Into a 10-mL volumetric flask was added 1.132 g (10.0 mmol, 1.00 M) of 3-cyanopropanoic acid methyl ester, 8.752 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1h), and the resulting 10 mL suspension stirred at 25° C. Samples (0.100 mL) were mixed with 0.900 mL of distilled water, centrifuged, then 0.180 mL of the 1:10 diluted supernatant was mixed with 0.020 mL of 0.750 M N-methylpropionamide (HPLC external standard solution). The resulting solution was analyzed by HPLC. After 6.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 6

Butanedioic acid monomethyl ester

Into a 10-mL volumetric flask was added 2.262 g (20.0 mmol, 2.00 M) of 3-cyanopropanoic acid methyl ester, 6.91 mL of potassium phosphate buffer (50 mM, pH 7.0), and 1.00 mL of a 50 wt % cell suspension (0.50 g wet cell weight, 0.12 g dry cell weight) of *Acidovorax facilis* 72W (ATCC 55746) cells in 0.35 M potassium phosphate buffer (pH 7.0, previously heat-treated at 50° C. for 1 h), and the resulting 10 mL suspension stirred at 25° C. Samples (0.100 mL) were mixed with 1.900 mL of distilled water, centrifuged, then 0.180 mL of the 1:20 diluted supernatant was mixed with 0.020 mL of 0.750 M N-methylpropionamide (HPLC external standard solution). The resulting solution was analyzed by HPLC. After 2.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 7

Immobilization of *A. facilis* 72W in carrageenan beads

Into a 250 mL media bottle equipped with magnetic stir bar and containing 64 g of water at 50° C. was slowly added 3.38 g of Pronova ISAGEL RG300 carrageenan with rapid stirring. The mixture was heated to 75–80° C. with rapid stirring until the carrageenan was completely dissolved, and the resulting solution cooled to 55–56° C. (gelling temperature ca. 52° C.) in a thermostated water bath. A suspension of 23.4 g of *A. facilis* 72W cells (wcw, 5.62 g dcw) in 21.56 g of 0.35 M sodium phosphate buffer (pH 7.3) was heated to 50° C. for 1hour to deactivate nitrile hydratase. The cell suspension at 50° C. was then added to the carrageenan solution at 55–56° C. with stirring, then the cell/carrageenan mixture was immediately added slowly to 450 mL of soybean oil at 50° C. with stirring using an overhead stirrer. After cell/carrageenan droplets of the desired size (ca. 1–3 mm in diameter) were produced in the oil by controlling the stirring rate, the temperature of the oil was reduced to 35° C. to gel the droplets, and the oil decanted from the resulting beads. The beads were suspended in 250 mL of 0.20 M potassium chloride (pH 7.3) at 25° C., and 0.25 g of 25 wt % glutaraldehyde in water was added and the beads mixed for 0.5 h. To the mixture was then added 1.0 g of 12.5 wt % polyethylenimine (average Mw ca. 750,000) in water, and the beads mixed for an additional hour at 25° C. The beads were then recovered by decantation of the reaction mixture and stored in 0.3 M ammonium bicarbonate (pH 7.0) at 5° C.

EXAMPLE 8

Butanedioic acid monomethyl ester produced using, immobilized *A. facilis* 72W

Into a 125 mL jacketed reaction vessel with overhead stirrer was placed 5.0 g of immobilized *A. facilis* 72W/carrageenan catalyst beads prepared as in Example 7, 90.8 mL of 50 mM potassium phosphate buffer (pH 7.0), and 4.19 mL (4.52 g, 0.40 M) of 3-cyanopropanoic acid methyl ester, and the mixture stirred at 25° C. Samples (0.100 mL) were mixed with 0.300 mL of distilled water, centrifuged, then 0.180 mL of the 1:4 diluted supernatant was mixed with 0.020 mL of 0.750 M N-methylpropionamide (HPLC external standard solution). The resulting solution was analyzed by HPLC. After 9.0 h, the conversion of 3-cyanopropanoic acid methyl ester was complete, and the yield (determined by HPLC) of butanedioic acid monomethyl ester was 100%, with no production of 3-cyanopropionic acid or butanedioic acid.

EXAMPLE 9

Hexanedioic acid monomethyl ester

Into a 10-mL volumetric flask was added 0.1616 g(1.01 mmol, 0.101 M) of 5-cyanopentanoic acid methyl ester, 9.65 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1 h), and the resulting 10 mL suspension stirred at 25° C. Samples (0.100 mL) were withdrawn and mixed with 0.300 mL of distilled water, centrifuged, then 0.180 mL of the 1:4 diluted supernatant was mixed with 0.020 mL of 0.750 M N-methylpropionamide (HPLC external standard solution). The resulting solution was analyzed by HPLC. After 4.0 h, the conversion of 5-cyanopentanoic acid methyl ester was complete, and the yield (determined by HPLC) of Hexanedioic acid monomethyl ester and hexanedioic acid were 99%, and 1%, respectively, with no production of 5-cyanopentanoic acid.

EXAMPLE 10

Hexanedioic acid monomethyl ester

Into a 10-mL volumetric flask was added 1.425 g (10.0 mmol, 1.00 M) of 5-cyanopentanoic acid methyl ester, 8.38 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1 h), and the resulting 10 mL suspension stirred at 25° C. Samples (0.100 mL) were withdrawn and mixed with 0.900 mL of distilled water, centrifuged, then 0.180 mL of the 1:10 diluted supernatant was mixed with 0.020 mL of 0.750 M N-methylpropionamide (HPLC external standard solution). The resulting solution was analyzed by HPLC. After 120 h, the conversion of 5-cyanopentanoic acid methyl ester was complete, and the yield (determined by HPLC) of hexanedioic acid monomethyl ester and hexanedioic acid were 97%, and 3%, respectively, with no production of 5-cyanopentanoic acid.

EXAMPLE 11

Propanedioic acid monoethyl ester

Into a 10 mL volumetric flask was added 0.1177 g (1.02 mmol, 0.102 M) of cyanoacetic acid ethyl ester, 9.689 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1 h), and the resulting 10 mL suspension stirred at 25° C. Samples (0.180 mL) were mixed with 0.020 mL of 0.750 M N-methylpropionamide (HPLC external standard solution). The resulting solution was analyzed by HPLC. After 5 h, the conversion of cyanoacetic acid ethyl ester was complete, and the yield (determined by HPLC) of propanedioic acid monoethyl ester was 100%, with no production of cyanoacetic acid or propanedioic acid.

EXAMPLE 12

Propanedioic acid monoethyl ester

Into a 10-mL volumetric flask was added 0.4619 g (4.00 mmol, 0.400 M) of cyanoacetic acid ethyl ester, 9.37 mL of potassium phosphate buffer (50 mM, pH 7.0), and 0.20 mL of a 50 wt % cell suspension (0.10 g wet cell weight, 0.024 g dry cell weight) of *Acidovorax facilis* 72W (ATCC 55746) cells in 0.35 M potassium phosphate buffer (pH 7.0, previously heat-treated at 50° C. for 1h), and the resulting 10 mL suspension stirred at 25° C. Samples (0.100 mL) were withdrawn and mixed with 0.300 mL of distilled water, centrifuged, then 0.180 mL of the 1:4 diluted supernatant was mixed with 0.020 mL of 0.750 M N-methylpropionamide (HPLC external standard solution). The resulting solution was analyzed by HPLC. After 25.5 h, the conversion of cyanoacetic acid ethyl ester was complete, and the yield (determined by HPLC) of propanedioic acid monoethyl ester was 100%, with no production of cyanoacetic acid or propanedioic acid.

EXAMPLE 13

Propanedioic acid monopropyl ester

Into a 10-mL volumetric flask was added 0.1271 g (1.00 mmol, 0.100 M) of cyanoacetic acid propyl ester, 9.689 mL of potassium phosphate buffer (50 mM, pH 7.0), and 0.20 mL of a 50 wt % cell suspension (0.10 g wet cell weight, 0.024 g dry cell weight) of Acidovorax facilis 72W (ATCC 55746) cells in 0.35 M potassium phosphate buffer (pH 7.0, previously heat-treated at 50° C. for 1h), and the resulting 10 mL suspension stirred at 25° C. Samples (0.180 mL) were mixed with 0.020 mL of 0.750 M N-methylpropionamide (HPLC external standard solution). The resulting solution was analyzed by HPLC. After 5 h, the conversion of cyanoacetic acid propyl ester was complete, and the yield (determined by HPLC and NMR) of propanedioic acid monopropyl ester was 100%, with no production of cyanoacetic acid or propanedioic acid.

EXAMPLE 14

1,4-Benzenedicarboxylic acid monomethyl ester

Into a 20-mL glass vial equipped with stirring bar was added 0.0252 g (0.155 mmol, 0.052 M) of 4-cyanobenzoic acid methyl ester, 2.67 mL of potassium pyrophosphate buffer (20 mM, pH 7.0), and 0.30 mL of a 50 wt % cell suspension (0.155 g wet cell weight, 37.3 mg dry cell weight) of *Acidovorax facilis* 72W (ATCC 55746) cells in 0.35 M potassium phosphate buffer (pH 7.0, previously heat-treated at 50° C. for 20 min ), and the resulting 3 mL suspension stirred at 25° C. After 25.5 h, the pH of the reaction mixture was adjusted to between 1.5 and 2.0 with 6.0 N HCl, then 9.0 mL of a mixture of acetonitrile (44% v/v) and methanol (56% v/v) was added and the resulting mixture filtered and analyzed by gas chromatography. The conversion of 4-cyanobenzoic acid methyl ester was complete, and the yield (determined by GC) of 1,4-benzenedicarboxylic acid monomethyl ester was 94%, with no production of 4-cyanobenzoic acid.

EXAMPLE 15

Butanedioic acid monomethyl ester

Into a 10-mL volumetric flask is added 0.4536 g (4.01 mmol, 0.401 M) of 3-cyanopropanoic acid methyl ester, 9.38 mL of potassium phosphate buffer (50 mM, pH 7.0), and 0.20 mL of a 50 wt % cell suspension (0.10 g wet cell weight, 0.024 g dry cell weight) of *Escherichia coli* SS1001 (ATCC PTA-1177) or *Escherichia coli* SW91 (ATCC PTA-1175) cells in 0.050 M potassium phosphate buffer (pH 7.0), and the resulting 10 mL suspension is stirred at 25° C. Samples (0.100 mL) are mixed with 0.300 mL of distilled water, centrifuged, then 0.180 mL of the 1:4 diluted supernatant is mixed with 0.020 mL of 0.750 M N-methylpropionamide (HPLC external standard solution). The resulting solution is analyzed by HPLC. At complete conversion of 3-cyanopropanoic acid methyl ester, the yield (determined by HPLC) of butanedioic acid monomethyl ester is expected to be about 100%, with no production of 3-cyanopropionic acid or butanedioic acid.

What is claimed is:

1. A process to prepare aliphatic or aromatic dicarboxylic acid monoesters from aliphatic or aromatic cyanocarboxylic acid esters comprising (a) contacting an aliphatic or aromatic cyanocarboxylic acid ester in an aqueous reaction mixture with an enzyme catalyst characterized by a chemoselective nitrilase activity derived from *Acidovorax facilis* 72W (ATTC #55746); and (b) isolating the aliphatic or aromatic dicarboxylic acid monoester produced in (a).

2. The process of claim 1 wherein the aliphatic cyanocarboxylic acid ester has the formula

where n=0 to 16, $R_1$ and $R_2$ for each $(CR_1R_2)$ unit are individually selected from the group consisting of hydrogen, hydroxyl, alkoxyl, aryloxyl, unsubstituted or substituted alkyl, unsubstituted or substituted alkenyl, unsubstituted or substituted alkylidene, unsubstituted or substituted alkylaryl, unsubstituted or substituted aryl, alkoxycarboxyl, and aryloxycarboxyl, and where $R_3$ is selected from the group consisting of unsubstituted or substituted alkyl, alkylaryl, and aryl.

3. The process of claim 1 wherein the aromatic cyanocarboxylic acid ester has the formula

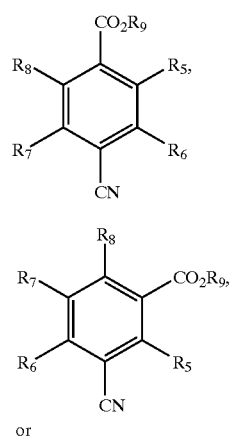

or

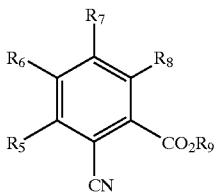

III where $R_5$, $R_6$, $R_7$, and $R_8$ are individually selected from the group consisting of hydrogen, hydroxyl, alkoxyl, aryloxyl, unsubstituted or substituted alkyl, unsubstituted or substituted alkenyl, unsubstituted or substituted alkylaryl, unsubstituted or substituted aryl, alkoxycarboxyl, and aryloxycarboxyl, and where $R_9$ is selected from the group consisting of unsubstituted or substituted alkyl, alkylaryl, and aryl.

4. The process of claim 1 wherein the enzyme catalyst is in the form of whole microbial cells, permeabilized microbial cells, one or more cell components of a microbial cell extract, partially purified enzyme(s), or purified enzyme(s).

5. The process of claim 4 wherein the enzyme catalyst is in the form of whole microbial cells selected from the group consisting of *Acidovorax facilis* 72-PF-15 (ATCC 55747), *Acidovorax facilis* 72-PF-17 (ATCC 55745), *Acidovorax facilis* 72W (ATCC 55746), and whole microbial cells transformed to express *Acidovorax facilis* 72W nitrilase activity.

6. The process of claim 5 wherein the transformed microbial cells having *Acidovorax facilis* 72W nitrilase activity are *Escherichia coli* SS1001 (ATCC PTA-1177) or *Escherichia coli* SW91 (ATCC PTA-1175).

7. The process of claim 5 wherein the enzyme catalyst in the form of whole microbial cells is immobilized in or on a soluble or insoluble support.

8. The process of claim 4 wherein the enzyme catalyst in the form of partially-purified or purified enzyme is immobilized in or on a soluble or insoluble support.

9. A chemoselective process to prepare aliphatic dicarboxylic acid monoesters from the corresponding aliphatic cyanocarboxylic acid ester comprising (a) contacting an aliphatic cyanocarboxylic acid ester having the formula

where n=0 to 16, $R_1$ and $R_2$ for each $(CR_1R_2)$ unit are individually selected from the group consisting of hydrogen, hydroxyl, alkoxyl, aryloxyl, unsubstituted or substituted alkyl, unsubstituted or substituted alkenyl, unsubstituted or substituted alkylidene, unsubstituted and substituted alkylaryl, unsubstituted or substituted aryl, alkoxycarboxyl, or aryloxycarboxyl, and where $R_3$ is selected from the group consisting of unsubstituted or substituted alkyl, alkylaryl, and aryl, in an aqueous reaction mixture with an enzyme catalyst characterized by a chemoselective nitrilase activity and selected from the group consisting of:

*Acidovorax facilis* 72W (ATCC 55746),
Acidovorax facilis 72-PF-15 (ATCC 55747),
Acidovorax facilis 72-PF-17 (ATCC 55745),
*Escherichia coli* SS1001 (ATCC PTA-1 177), and
*Escherichia coli* SW91 (ATCC PTA-1175), and (b) isolating the aliphatic dicarboxylic acid monoester produced in (a).

10. A chemoselective process for preparing aromatic dicarboxylic monoesters from the corresponding aromatic cyanocarboxylic acid ester comprising (a) contacting an aromatic cyanocarboxylic acid ester having the formula

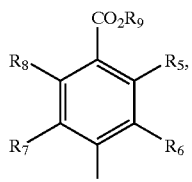

I

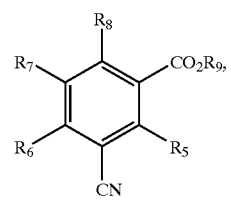

II or

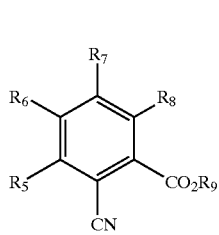

III where $R_5$, $R_6$, $R_7$, and $R_8$ are individually selected from the group consisting of hydrogen, hydroxyl, alkoxyl, aryloxyl, unsubstituted or substituted alkyl, unsubstituted or substituted alkenyl, unsubstituted or substituted alkylaryl, unsubstituted or substituted aryl, alkoxycarboxyl, and aryloxycarboxyl, and where $R_9$ is selected from the group consisting of unsubstituted or substituted alkyl, alkylaryl, and aryl, in an aqueous reaction mixture with an enzyme catalyst characterized by a chemoselective nitrilase activity and selected from the group consisting of:

Acidovorax facilis 72W (ATCC 55746),
Acidovorax facilis 72-PF-15 (ATCC 55747),
Acidovorax facilis 72-PF-17 (ATCC 55745), and
*Escherichia coli* SS1001(ATCC PTA-1177), and
EscherichiaColi SW91 (ATCC PTA-1175), and (b) isolating the aromatic dicarboxylic acid monoester produced in (a).

11. The process of claims 9 or 10 wherein the enzyme catalyst is in the form of whole microbial cells, permeabilized microbial cells, one or more cell components of a microbial cell extract, or partially purified enzyme(s) or purified enzyme(s).

12. The process of claim 11 wherein the enzyme catalyst is in the form of whole microbial cells immobilized in or on a soluble or insoluble support.

13. The process of claim 11 wherein the enzyme catalyst is in the form of partially purified enzyme(s) or enzyme(s) immobilized in or on a soluble or insoluble support.

14. A regioselective and chemoselective process to prepare aliphatic or aromatic dicarboxylic acid monoesters from aliphatic or aromatic cyanocarboxylic acid esters comprising:

(a) heating a suspension of *Acidovorax facilis* 72W (ATCC 55746) whole cells, characterized by 1) a regioselective and chemoselective nitrilase activity and 2) a non-regioselective nitrile hydratase and amidase activity, to a temperature of about 35° C. to 70° C. for between 10 and 120 minutes whereby the non-regioselective nitrile hydratase and amidase activity is destroyed and the regioselective nitrilase activity is preserved;

(b) optionally, immobilizing the whole microbial cell catalyst in or on a soluble or insoluble support;

(c) contacting an aliphatic or aromatic cyanocarboxylic acid ester in an aqueous reaction mixture with the whole microbial cell catalyst; and (d) isolating the aliphatic or aromatic dicarboxylic acid monoester produced in (c).

15. The regioselective and chemoselective process of claim 14 to prepare aliphatic dicarboxylic acid monoesters wherein (a) the aliphatic cyanocarboxylic acid ester has the formula

where n=0 to 16, $R_1$ and $R_2$ for each $(CR_1R_2)$ unit are individually selected from the group consisting of hydrogen, hydroxyl, alkoxyl, aryloxyl, unsubstituted or substituted alkyl, unsubstituted or substituted alkenyl, unsubstituted or substituted alkylidene, unsubstituted and substituted alkylaryl, unsubstituted or substituted aryl, alkoxycarboxyl, or aryloxycarboxyl, and where $R_3$ is selected from the group consisting of unsubstituted or substituted alkyl, alkylaryl, and aryl, and (b) the corresponding aliphatic dicarboxylic acid monoester is isolated.

16. The regioselective and chemoselective process of claim 14 to prepare aromatic dicarboxylic monoesters wherein (a) the aromatic cyanocarboxylic acid ester has the formula

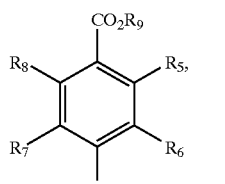

I

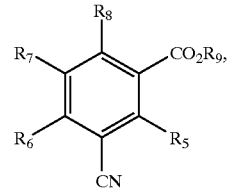

II or

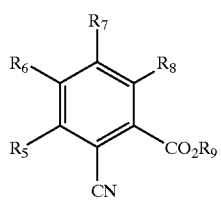

III where $R_5$, $R_6$, $R_7$, and $R_8$ are individually selected from the group consisting of hydrogen, hydroxyl, alkoxyl, aryloxyl, unsubstituted or substituted alkyl, unsubstituted or substituted alkenyl, unsubstituted or substituted alkylaryl, unsubstituted or substituted aryl, alkoxycarboxyl, and aryloxycarboxyl, and where $R_9$ is selected from the group consisting of unsubstituted or substituted alkyl, alkylaryl, and aryl, and (b) the corresponding aromatic dicarboxylic acid monoester is isolated.

17. A regioselective and chemoselective process to prepare aliphatic or aromatic dicarboxylic acid monoesters from aliphatic or aromatic cyanocarboxylic acid esters comprising:

(a) optionally, immobilizing a whole microbial cell catalyst transformed to express *Acidovorax facilis* 72W nitrilase enzyme activity in or on a soluble or insoluble support;

(b) contacting an aliphatic or aromatic cyanocarboxylic acid ester in an aqueous reaction mixture with the whole microbial cell catalyst of step (a); and (c) isolating the aliphatic or aromatic dicarboxylic acid monoester produced in (b).

18. The regioselective and chemoselective process of claim 17 to prepare aliphatic dicarboxylic acid monoesters from the corresponding aliphatic cyanocarboxylic acid ester wherein (a) the aliphatic cyanocarboxylic acid ester has the formula

where n=0 to 16, $R_1$ and $R_2$ for each $(CR_1R_2)$ unit are individually selected from the group consisting of hydrogen, hydroxyl, alkoxyl, aryloxyl, unsubstituted or substituted alkyl, unsubstituted or substituted alkenyl, unsubstituted or substituted alkylidene, unsubstituted and substituted alkylaryl, unsubstituted or substituted aryl, alkoxycarboxyl, or aryloxycarboxyl, and where $R_3$ is selected from the group consisting of unsubstituted or substituted alkyl, alkylaryl, and aryl, and (b) the corresponding aliphatic dicarboxylic acid monoester is isolated.

19. The regioselective and chemoselective process of claim 17 to prepare aromatic dicarboxylic monoesters from the corresponding aromatic cyanocarboxylic acid ester wherein (a) the aromatic cyanocarboxylic acid ester has the formula

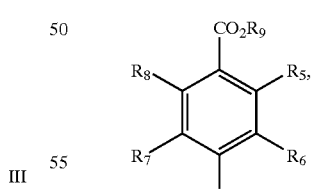

I

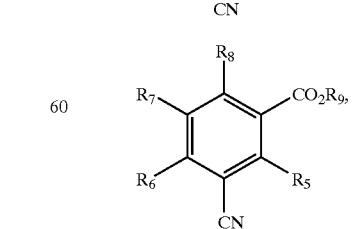

II or

-continued

III

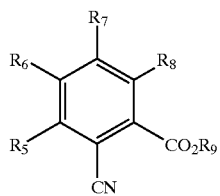

where $R_5$, $R_6$, $R_7$, and $R_8$ are individually selected from the group consisting of hydrogen, hydroxyl, alkoxyl, aryloxyl, unsubstituted or substituted alkyl, unsubstituted or substituted alkenyl, unsubstituted or substituted alkylaryl, unsubstituted or substituted aryl, alkoxycarboxyl, and aryloxycarboxyl, and where $R_9$ is selected from the group consisting of unsubstituted or substituted alkyl, alkylaryl, and aryl, and (b) the corresponding aromatic dicarboxylic acid monoester is isolated.

20. The process of claims 17 or 18 wherein the whole microbial cell catalyst transformed to express *Acidovorax facilis* 72W nitrilase enzyme activity is selected from the group consisting of *Escherichia coli* SS1001 (ATCC PTA-1177) and *Escherichia coli* SW91 (ATCC PTA-1175).

* * * * *